(12) United States Patent
Cereda et al.

(10) Patent No.: US 6,281,218 B1
(45) Date of Patent: Aug. 28, 2001

(54) BENZIMIDAZOLONE DERIVATIVES HAVING MIXED SEROTONIN AND DOPAMINE RECEPTORS AFFINITY

(75) Inventors: Enzo Cereda, Novi Ligure; Maura Bignotti, Milan; Giovanni Battista Schiavi, Asola, all of (IT)

(73) Assignee: Ingelheim Italia S.p.A., Firenze (IT)

(*) Notice: Subject to any disclaimer, the term of this patent is extended or adjusted under 35 U.S.C. 154(b) by 0 days.

(21) Appl. No.: 09/634,120

(22) Filed: Aug. 8, 2000

(30) Foreign Application Priority Data

Sep. 22, 1999 (IT) .............................. MI99A1964

(51) Int. Cl.$^7$ ...................... A61K 31/496; C07D 403/06

(52) U.S. Cl. ..................................... 514/254.06; 544/370

(58) Field of Search ....................... 544/370; 514/254.06

(56) References Cited

U.S. PATENT DOCUMENTS 5,576,318 * 11/1996 Bietti et al. .......................... 544/370

OTHER PUBLICATIONS

"Protective Groups in Organic Synthesis" by Theodora W. Greene, pp. 10–17, 1981.*

* cited by examiner

*Primary Examiner*—Emily Bernhardt
(74) *Attorney, Agent, or Firm*—R. P. Raymond; T. X. Witkowski

(57) ABSTRACT

Compounds of general formula (I)

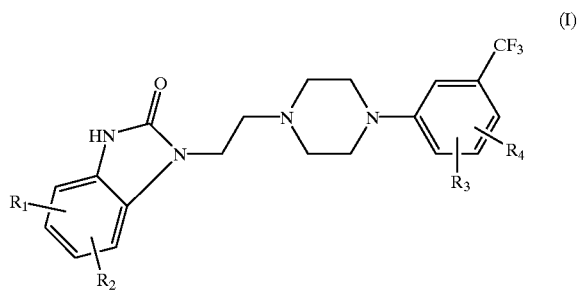

wherein $R_1$, $R_2$, $R_3$, and $R_4$ denote hydrogen or hydroxy with the proviso that $R_1$, $R_2$, $R_3$, and $R_4$ cannot simultaneously represent hydrogen, processes for their preparation of the compounds of general formula (I), and their use as pharmaceuticals.

14 Claims, No Drawings

BENZIMIDAZOLONE DERIVATIVES HAVING MIXED SEROTONIN AND DOPAMINE RECEPTORS AFFINITY

The present invention relates to novel pharmacologically active benzimidazolone derivatives and their addition salts which bind the serotonin and dopamine receptors, to their preparation and their use for therapeutic purposes. These compounds, owing to their pharmacological activity, are useful in the treatment of CNS disorders.

BACKGROUND OF THE INVENTION

Serotonin (5-HT) and Dopamine recognize several well-defined cell surface receptors. Among these, $5\text{-}HT_{1A}$, $5\text{-}HT_{2A}$, and $D_4$ at which serotonin and dopamine, respectively, have high affinity, are known to be implicated in many Central Nervous System (CNS) disorders such as depression, anxiety, schizophrenia, Parkinson's disease, and neurodegenerative diseases.

In the previous art, several classes of compounds able to interfere with the neurotransmission at serotonin or dopamine receptor subtypes are known. Particularly, derivatives based on the core structure of the arylpiperazine and benzimidazolone have been described (e.g., GB 2,023,594; U.S. Pat. No. 3,472,854; U.S. Pat. No. 4,954,503; and WO 98/33784), and targeted both to generic serotonin or dopamine receptors and to a specific receptor subtype. In another patent (U.S. Pat. No. 5,576,318), compounds based both on the benzimidazolone and phenyl piperazine structures are described: in this latter case the described affinities are limited to $5\text{-}HT_{1A}$ and $5\text{-}HT_{2A}$ receptor subtypes.

DETAILED DESCRIPTION OF THE INVENTION

Here we describe, and this is the object of the present invention, new hydroxylated derivatives based on the benzimidazolone phenyl piperazine structure. Surprisingly it was discovered that the compounds according to this invention possess an interesting affinity profile at the said serotonin and dopamine receptor subtypes: indeed, some of them have a high and preferential affinity at a given site (e.g., $5\text{-}HT_{1A}$, $5\text{-}HT_{2A}$, or $D_4$), whereas some other have a mixed affinity at all the said receptors.

Owing to their peculiar profile, the present compounds may play a role in the regulation of neurotransmission at the serotonin and/or the dopamine sites an:d thus may be of value in the treatment of those diseases where an altered functioning of neurosignal transmission is present. Examples of these CNS disorders include depression, schizophrenia, Parkinson's disease, anxiety, sleep disturbances, sexual and mental disorders, and age-associated memory impairment.

According to the present invention, we provide compounds of general formula (I)

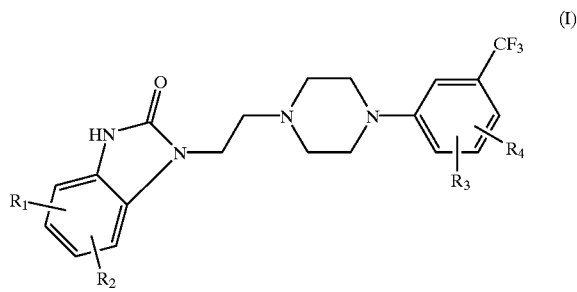

wherein:
  $R_1$, $R_2$, $R_3$, and $R_4$ denote hydrogen or hydroxy with the proviso that $R_1$, $R_2$, $R_3$, and $R_4$ cannot simultaneously represent hydrogen.

Preferred compounds according to the invention are those of general formula (I) wherein two or three of the four radicals $R_1$, $R_2$, $R_3$, and $R_4$ denote hydrogen.

Also preferred are compounds of general formula (I) wherein one of the radicals $R_1$, $R_2$, $R_3$, and $R_4$ denotes hydroxy, while the other radicals represent hydrogen.

Of particular interest are compounds selected from the group consisting of:

(a) 5-hydroxy-1-{2-[4-(3-trifluoromethylphenyl)piperazin-1-yl]-ethyl}-1,3-dihydrobenzimidazol-2-one;

(b) 6-hydroxy-1-{2-[4-(3-trifluoromethylphenyl)piperazin-1-yl]-ethyl}-1,3 -dihydrobenzimidazol-2-one;

(c) 4-hydroxy-1-{2-[4-(3-trifluoromethylphenyl)piperazin-1-yl]-ethyl}-1,3-dihydrobenzimidazol-2-one;

(d) 7-hydroxy-1-{2-[4-(3-trifluoromethylphenyl)piperazin-1-yl]-ethyl}-1,3-dihydrobenzimidazol-2-one;

(e) 1-{2-[4-(4-hydroxy-3-trifluoromethylphenyl)piperazin-1-yl]-ethyl}-1,3-dihydrobenzimidazol-2-one;

(f) 1-{2-[4-(3-hydroxy-5-trifluoromethylphenyl)piperazin-1-yl]-ethyl}-1,3-dihydrobenzimidazol-2-one;

(g) 1-{2-[4-(2-hydroxy-5-trifluoromethylphenyl)piperazin-1-yl]-ethyl}-1,3-dihydrobenzimidazol-2-one; and (h) 1-{2-[4-(2-hydroxy-3-trifluoromethylphenyl)piperazin-1-yl]-ethyl}-1,3-dihydrobenzimidazol-2-one.

For pharmaceutical use, the compounds of general formula (I) may be used either as free base or in the form of physiologically acceptable acid addition salts. The term "acceptable acid addition salts" includes both organic and inorganic acids such as maleic, citric, tartaric, methanesulphonic, acetic, benzoic, succinic, gluconic, isethionic, glycinic, lactic, malic, mucoic, glutamic, sulfamic, and ascorbic acid; inorganic acids include hydrochloric, hydrobromic, nitric, sulfuric, or phosphoric acid.

The compounds of general formula (I) may be conveniently prepared by a variety of synthetic processes analogous to those known in the art using conventional methods and starting from suitable intermediates in which the hydroxy function (generally in the form of a methoxy precursor group) is inserted in a well defined position, and suitable for originating the final target compound. When a masked (i.e., protected) hydroxy function is used throughout all the synthetic process, the hydroxy function is generated in the last step as exemplarily outlined in Scheme 1.

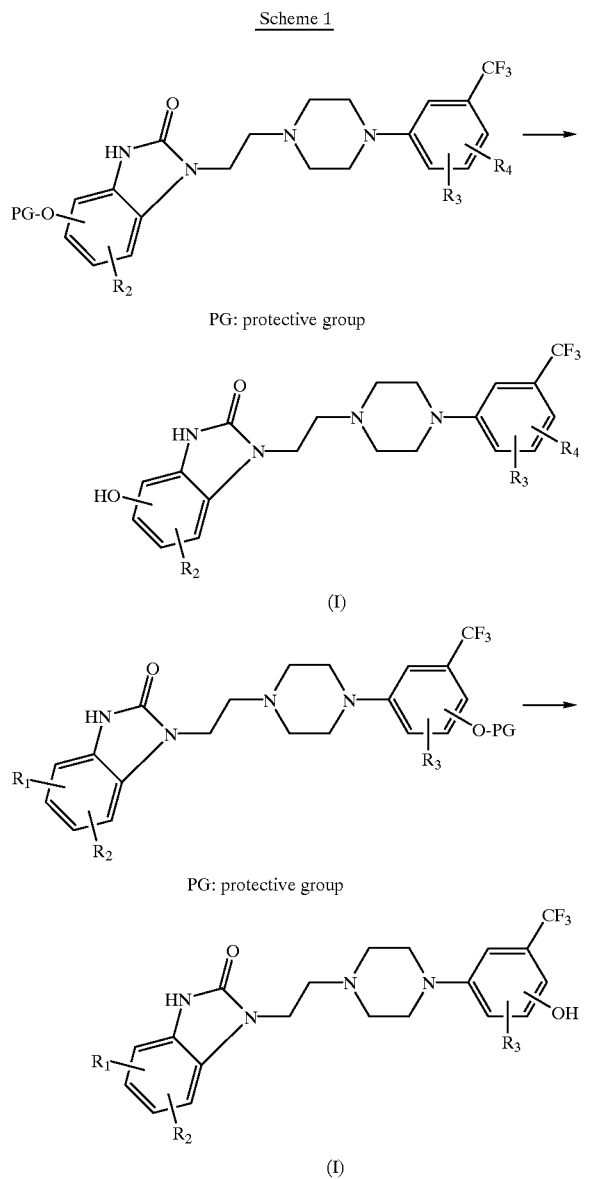

As protective groups conventional ether protective groups are applicable (e.g., methyl, methoxymethyl, benzyl). The preferred protecting group according to the invention is the methyl ether. The deprotection of the hydroxy group can be easily carried out by conventional known procedures. In case of the preferred protecting group (methoxy), the deprotection is achieved by treatment with strong aqueous acids such as 48% hydrobromic acid at high temperatures or alternatively by treatment with boron derivatives, such as $BBr_3$, at low temperatures in chlorinated solvents such as methylene dichloride.

As mentioned before, the compounds of formula (I) according to the present invention, surprisingly show interesting pharmacological properties owing to their different profile at the serotonin or dopamine receptor subtypes, such as $5\text{-HT}_{1A}$, $5\text{-HT}_{2A}$ and $D_4$. The biochemical profile of the compounds was assessed by evaluating their affinity for the $5\text{-HT}_{1A}$, $5\text{-HT}_{2A}$ and $D_4$ receptors, according to the methods described below.

Receptor Binding Studies

Binding studies were carried out to determine the affinity of the compounds for $5\text{-HT}_{1A}$, $5\text{-HT}_{2A}$, and $D_4$ receptors $5\text{-HT}_{1A}$ Receptor Tissue preparation:

Male Sprague-Dawley rats (200–250 g) were used. The hippocampus taken from these animals was homogenized in 10 volumes of ice cold 50 mM TIUS buffer (pH 7.4). The homogenate was diluted 1:400 (w:v) in the same buffer to have a final protein concentration of about 200 µg/ml, filtered and incubated at 37° C. for 10 minutes before use.

Binding Assay:

Displacement experiments were performed by incubating the homogenate (980 µl) in the presence of [$^3$H]-8-OH-DPAT (10 µl; 1.0–1.2 nM) and different concentrations of the test compounds dissolved in DMSO (10 µl), at 30° C. for 15 minutes (final volume: 1 ml). Nonspecific binding was determined in the presence of 10 µM 5-HT (10 µl). The reaction was stopped by rapid filtration through Inotech IH 201 filters using an Inotech Cell Harvester. The radioactivity was counted by liquid scintillation spectrometry.

$5\text{ HT}_{2A}$ Receptor

Tissue preparation:

Male Sprague-Dawley rats (200–250 g) were used. Cerebral cortex was homogenized in 10 volumes of ice cold 0.32 M sucrose. After the centrifugation of the homogenate (1,000×g for 10 minutes) the supernatant was then recentrifuged at 48,000×g for 15 minutes. The resulting pellet was suspended in 10 volumes of 50 mM TRIS buffer (pH 7.4), incubated at 37° C. for 10 minutes and recentrifuged at 48,000 × g for 15 minutes. The residue was then resuspended in 10 volumes of 50 mM TRIS buffer (pH 7.4).

Binding Assay:

The tissue was diluted 1:100 (w:v) in 50 mM TRIS buffer (pH 7.4) to have a final concentration of about 200 µg/ml. Displacement experiments were performed by incubating the homogenate (980 µl) in the presence of [$^3$H]-Ketanserine (10 µl; 0.5–0.6 nM) and different concentrations of the test compounds dissolved in DMSO (10 µl) at 37° C. for 10 minutes (final volume: 1 ml). Nonspecific binding was determined in the presence of 100 µM Methysergide (10 µl). The reaction was stopped by rapid filtration through Inotech IH 201 filters using an Inotech Cell Harvester. The radioactivity was counted by liquid scintillation spectrometry.

$D_4$ Receptor

Cell culture:

Cells were grown in monolayer at 37° C. in 95% air/5% $CO_2$ in Dulbecco's Modified Eagle Medium (DMEM) supplemented with 7.5% (v/v) heat-inactivated fetal bovine serum (FBS), 2.5% (v/v) heat-inactivated horse serum donor herd, 2% of a stock solution containing 5000 I.U./ml penicillin and 5000 µg/ml streptomycin, 1% (v/v) of a solution MEM containing non-essential amino acid, 2 mM glutamine ind 200 µg/ml geneticin. Cells were passaged twice a week using a trypsin/EDTA solution and the split rate was 1:4. Cells were not subcultured more than 17 times.

Preparation of cell membranes:

The cells grown to confluence were washed twice with Dulbecco's PBS buffer and were detached adding VERSENE (PBS containing 0.2 g/l EDTA) for 10 minutes at 37° C. The cell suspension was centrifuged at 1,000 rpm for 10 minutes and the pellet was harvested in DMEM with 10% DMSO and stored at −80° C. Before use, cells were thawed, centrifuged at 1,000 rpm for 10 minutes and the pellet was resuspended in PBS. The cells were centrifuged again at 270×g for 10 minutes at 4° C. and the pellet was resuspended in a lysis buffer (10 mM Tris-HCl pH 7.4, 5 mM Na$_2$EDTA and protease inhibitors) and incubated for 30 minutes on ice. Cells were homogenized with an Ultra Turrax homogenizer. Unbroken cells and nuclei were removed by an initial centrifugation at 270×g for 10 minutes at 4° C. and crude membranes were collected from the supernatant by a 60 minute spin at 130,000×g. The pelleted membranes were resuspended in the same lysis buffer with 20 strokes by a Potter homogenizer. The final cell membrane suspension, corresponding to about 1×10$^7$ original cells/ml, was aliquoted and immediately frozen at −80° C.

Membrane preparation:

D$_4$ receptor binding studies were carried out in membranes from CHO cells prepared as above. The membranes were dilute in incubation buffer (50 ml/ TRIS-HCl pH 7.4, 5 mM MgCl$_2$·6H$_2$O, 5 mM KCl, 1.5 mM CaCl$_2$·2H$_2$O, 5 mM EDTA) according to their receptor density.

Binding assay:

Displacement experiment were performed in 1000 μl total volume incubating the membranes (980 μl) in the presence of [$^3$H]-YM 09151-2 (10 μl; 0.15–0.25 nM) and different concentrations of the test compounds dissolved in DMISO (10 μl) at 27° C. for two hours. Nonspecific binding was determined in the presence of 10 μM of Clozapine (10 μl). The reaction was stopped by rapid filtration through Inotech IH 201 filters (pre-soaked in 0.1% polyethyleneimine) using an Inotech Cell Harvester. The radioactivity was counted by liquid scintillation spectrometry.

Data analysis:

The affinity values ($K_i$) for the compounds were obtained by a nonlinear least squares regression analysis on the basis of a one binding site model. The values were corrected on the basis of the radioligand occupancy on the receptors according to the equation: $K_i = IC_{50}/(1+[C]/K_d)$, where [C] and $K_d$ represent the concentration and the dissociation constant of the used radioligands ([$^3$H]-8-OH-DPAT for the 5-HT$_{1A}$ binding, [$^3$H]-Ketanserine for the 5-HT$_{2A}$ binding and [$^3$H]-YM 09151-2) for the D$_4$ binding, respectively).

The following table (Table I) collects the affinity values ($K_i$, nM) at the said receptors of the new compounds.

TABLE I $K_i$ (nM) for 5-HT$_{1A}$, 5-HT$_{2A}$, and D$_4$ receptors

| Compound | 5-HT$_{1A}$ (rat hippocampus tissue) | 5-HT$_{2A}$ (Rat cortex tissue) | D$_4$ (CHO cell membranes) |
|---|---|---|---|
| 1 | 40.8 | 58.5 | 287 |
| 2 | 333 | 33.8 | 804 |
| 3 | 15.4 | 43.8 | 33.9 |
| 4 | 1590 | 23.8 | 652 |
| 5 | 369 | 705 | 17.8 |
| 6 | 156 | 328 | 24.8 |
| 7 | >10000 | 4436 | — |

As a further feature of the present invention there are provided pharmaceutical compositions comprising as an active ingredient at least one compound of formula (I), as before defined, or a physiologically acceptable addition salt thereof in addition with one or more pharmaceutical carrier, diluents or excipients. For pharmaceutical administration, the compounds of general formula (I) and their physiologically acceptable acid addition salts may be incorporated into the conventional pharmaceutical preparation in solid, liquid, or spray form. The composition may, for example, be presented in a form suitable for oral, rectal, parenteral administration or for nasal inhalation: preferred forms include, for example, capsules, tablets, coated tablets, ampoules, suppositories, and nasal spray.

The active ingredient may be incorporated in excipients or carriers conventionally used in pharmaceutical compositions such as, for example, talc, arabic gum, lactose, gelatine, magnesium stearate, corn starch, aqueous or nonaqueous vehicles, polyvinyl pyrrolidone, semisynthetic glycerides of fatty acids, benzalkonium chloride, sodium phosphate, EDTA, or polysorbate 80.

In case it is desired to further increase the solubility of the compounds of general formula (I) or of their physiologically acceptable salts, surfactants, nonionic surfactants such as PEG 400, cyclodextrin, metastable polymorphs, and inert adsorbents, such as bentonite, may be incorporated. Furthermore some techniques may be employed by preparing for example, eutectic mixtures and/or solid dispersion by using mannitol, sorbitol, saccharose, succinic acid, or physically modified forms by using hydrosoluble polymers, PVP, or PEG 4000–20,000.

The compositions are advantageously formulated in dosage units, each dosage unit being adapted to supply a single dose of the active ingredient. Each dosage unit may conveniently contain from 0.01 mg to 100 mg, preferably from 0.1 to 50 mg.

EXPERIMENTAL

The following examples illustrate the preparation of compounds according to the invention. It should be understood that the invention is not limited to the given examples of chemical methods and processes for the preparation of the substances, as other conventional methods well known to those skilled in the art, are suitable too.

DESCRIPTION 1

2-Bromo-N-(4-methoxy-2-nitrophenyl)acetamide

A solution of 2-bromoacetylbromide (17.9 ml; 0.20 moles) in CH$_2$Cl$_2$ (30 ml) was slowly added to a mixture of 4-methoxy-2-nitroaniline (30 g; 0.18 moles) and triethylamine (28 ml; 0.2 moles) in CH$_2$Cl$_2$ (300 ml). The reaction mixture was stirred at room temperature overnight, then poured into water. The aqueous layer was extracted with additional CH$_2$Cl$_2$, dried over MgSO$_4$ and evaporated under vacuum. The crude product was crystallized from a 7/3 Et$_2$O/EtOH mixture to give the title compound as a white solid. 31.5 g; m.p. 94–98° C.

DESCRIPTION 2

N-(4-Methoxy-2-nitrophenyl)-2-[4-(3-trifluoromethylphenyl)piperazin-1-yl]acetamide To a mixture of 2-bromo-N-(4-methoxy-2-nitrophenyl) acetami(le (13 g; 0.045 mol) and Na$_2$CO$_3$ (4.8 g) in anhydrous ethanol, 1-(3-trifluoromethylphenyl)piperazine (8.22 ml; 0.045 mol) was added dropwise. The mixture was stirred at room temperature overnight. The solvent was evaporated, the residue was dissolved into toluene and washed with water. From the evaporated organic layer, a crude solid was obtained. This was crystallized from a 9/1 Et$_2$O/EtOH mixture to give the title compound as a yellow solid. 10.7 g; m.p. 98–100° C.

According to the above-described procedure, the following compounds were prepared:

6-methoxy-1-{2-[4-(3-trifluoromethyl)phenylpiperazin-1-yl]ethyl}2,3-dihydro-2-oxo-1H-benzimidazole The reaction mixture was refluxed for 10 hours in the presence of a catalytic amount of KI. The title compound was recrystallized from 95% EtOH to give a white solid. m.p. 208–210° C.

2-methoxy-6-{2-[4-(3-trifluoromethylphenyl)piperazin-1-yl]acetylamino}phenyl)-Carbamic Acid Benzyl Ester The reaction mixture was heated at 100° C. for 3 hours in anhydrous DMF in the presence of a catalytic amount of KI. The title compound was crystallized from diethyl ether to give a white solid. m.p. 153–155° C.

7-methoxy-1-{2-[4-(3-trifluoromethylphenyl)piperazin-1-yl]ethyl}-1,3-dihydro-benzimidazol-2-one The reaction mixture was heated at 100° C. for 3 hours in anhydrous DMF in the presence of a catalytic amount of KI. The title compound was recrystallized from ethyl acetate and used without further purification.

1-{2-[4-(4-methoxy-3-trifluoromethylphenyl)piperazin-1-yl]ethyl}-1,3-dihydro-benzimidazol-2-one The reaction mixture was heated for 8 hours in DMF. The title compound was purified by flash chromatography (silica gel; eluent: $CH_2Cl_2$/MeOH/$NH_4OH$ 95:5:0.5)

1-{2-[4-(3-methoxy-5-trifluoromethylphenyl)piperazin-1yl] ethyl}-1,3-dihydro-benzimidazol-2-one The reaction mixture was heated for 6 hours in DMF. The title compound was crystallized from 95% EtOH as hydrochloride salt.

DESCRIPTION 3

4-methoxy-N-1-{2-[4-(3-trifluoromethylphenyl) piperazin-1-yl]ethyl}benzene-1,2-diamine To a solution of N-(4-methoxy-2-nitrophenyl)-2-[4-(3-trifluoromethylphenyl)piperazin-1-yl]acetamide (9 g; 0.021 mol) in tetrahydrofuran (THF), a 1 M solution of $BH_3$ in THF (168 ml, 0.168 mol) was added dropwise while keeping the temperature at 10–15° C. The solution was heated at 50° C. for 4 hours and stirred at room temperature overnight. The reaction was acidified to pH 2 with 10% aqueous HCl and heated at 60° C. for 1 hour, then it was cooled and basified to pH 9 with $Na_2CO_3$. The product was extracted from the aqueous phase with $CH_2Cl_2$ and purified by flash chromatography on silica gel (eluent: $CH_2Cl_2$/MeOH/$NH_4OH$ 95:5:0.5) to give the title compound as a white solid. 2.2 g; m.p. 57–60° C.

According to the above described procedure, additionally the following compound was prepared:

3-methoxy-N-1-{2-[4-(3-trifluoromethylphenyl) piperazin-1-yl]ethyl}benzene-1,2-diamine

DESCRIPTION 4

5-methoxy-1-{2-[4-(3-trifluoromethylphenyl)piperazin-1-yl]ethyl}-1,3-dihydro-benzimidazol-2-one To a solution of trichloromethyl chloroformate (0.12 ml, 1.1 inmoles) a solution of 4-methoxy-N-1{2-[4-(3-trifluoromethylphenyl)piperazin-1-yl]ethyl}benzene-1,2-diamine (0.4 g; 1.0 mmol) and triethylamine (0.14 ml; 1.1 mmol) in $CH_2Cl_2$, was added dropwise keeping the temperature at 25° C. The mixture was stirred at room temperature for 3 hours and a precipitate was formed. The crude solid was filtered off and recrystallized from isopropanol to give the title compound as the hydrochloride salt. 0.02 g; m.p. 212–216° C. (dec.).

According to the above described procedure, the following compounds were prepared:

5-methoxy-2-oxo-2,3-dihydrobenzimidazole-1-carboxylic acid-ethyl ester

The title compound was obtained from extraction in organic solvent ($CH_2Cl_2$) and recrystallization from isopropanol. White solid. m.p.180–183° C.

4-methoxy-1-{2-[4-(3-trifluoromethylphenyl)piperazin-1-yl]ethyl}-1,3-dihydro-benzimidazol-2-one The crude compound was used without further purification.

4-methoxy-1,3-dihydrobenzimidazol-2-one

Brown solid. The crude compound was used without further purification.

DESCRIPTION 5

(4-methoxy-2-nitrophenyl)carbamic Acid Ethyl Ester

To a cooled solution of 4-methoxy-2-nitroaniline (25 g; 0.15 mol) in pyridine (370 ml), ethyl chloroformate (17.8 ml; 0.18 mol) was added dropwise. The mixture was refluxed for 10 hours, then cooled and poured into ice-water. The precipitated solid was collected and purified by flash chromatography (silica gel, eluent: hexane/diethyl ether 85:15) to yield the title compound as a yellow solid. 7.3 g; m.p. 56–57° C.

DESCRIPTION 6

(4-methoxy-2 aminophenyl)carbamic acid ethyl ester

A solution of (4-methoxy-2-nitrophenyl)carbamic acid ethyl ester (7.3 g; 0.03 mol) in 95% EtOH (500 ml), was hydrogenated at room temperature and pressure in the presence of 10% aqueous HCl (13 ml) and 10% Pd/C (0.35 g). When the theoretical amount of hydrogen was taken up, the catalyst was filtered off and the solution was evaporated to dryness to give the title compound (5 g) after crystallization from $Et_2O$/EtOH (85:15). The compound was used without further purification.

According to the above described procedure, the following compounds were prepared:

3-methoxybenzene-1,2-diamine

The compound was used without further purification.

4-methoxy-3-trifluoromethylphenylamine

The compound was used without further purification.

2-amino-4-trifluoromethylphenol

Light brown solid; m.p. 115° C.

DESCRIPTION 7

3-(2-chloroethyl)-5-methoxy-2-oxo-2,3-dihydrobenzimidazole-1-carboxylic Acid Ethyl Ester A mixture of 5-methoxy-2-oxo-2,3-dihydrobenzimidazole-1-carboxylic acid ethyl ester and 80% NaH (0.38 g; 0.013 mol) in anhydrous DMF was stirred 20 minutes at room temperature. Then 1-bromo-2-chloroethane (1.1 ml; 0.013 moles) was added and the solution was stirred overnight. After cooling, the reaction mixture was poured into water and the separated oil was extracted into ethyl acetate. The organic layer was dried over $MgSO_4$ and evaporated under vacuum to give the crude title compound which was crystallized with diisopropyl ether. White solid. 1.35 g; m.p. 116–118° C.

According to the above described procedure, the following compound was additionally prepared.

1-(2-chloroethyl)-7-methoxy-1,3-dihydrobenzimidazol-2-one

The reaction mixture was treated with aqueous KOH for 4 hours to cleave the 1-carboxylic acid phenylester and the title compound was extracted in ethyl acetate and used without further purification.

DESCRIPTION 8

(2-methoxy-6-nitrophenyl)carbamic Acid Benzyl Ester

To a solution of 2-methoxy-6-nitroaniline (2g; 0.0119 moles) in anhydrous THF (20 ml), trichloroethyl chloroformate (1.43 ml; 0.01189 moles) was added dropwise. The reaction was heated for 45 minutes at 60° C., the solvent was then removed under vacuum and the crude residue was dissolved in dioxane (20 ml). To this solution, benzyl alcohol (2.46 ml; 0.0237 mmoles) was added and the reaction mixture was refluxed for 8 hours. The solvent was then removed under vacuum and the crude residue was poured into diluted 10% HCl. The title compound was extracted into ethyl ether. The crude brown oil was crystallized with diisopropyl ether to give a light brown solid. 1.9 g; m.p. 78–80° C.

DESCRIPTION 9
(2-Amino-6-methoxyphenyl)carbamic Acid Benzyl Ester

A mixture of (2-methoxy-6-nitrophenyl) carbamic acid benzyl ester (17.5 g; 0.058 mol) and $SnCl_2 \cdot 2H_2O$ (65.3 g; 0.29 mol) in anhydrous ethanol, was heated at 70° C. for 2 hours. The solvent was then removed under vacuum and the residue was acidified with 10% aqueous HCl. The title compound was extracted with ethyl acetate and washed with diluted aqueous $K_2CO_3$. The precipitated solid was filtered off, the organic layer was dried over $MgSO_4$ and evaporated under vacuum to give the title compound after crystallization with n-hexane. The compound was used without further purification. Yellow solid; 9.6 g.

DESCRIPTION 10
[2-(2-Chloroacetylamino)-6-methoxyphenyl]carbamic Acid Benzyl Ester To a cool solution of (2-amino-6-methoxyphenyl) carbamic acid benzyl ester (9.5 g; 34.9 mmol) and triethylamine (5.8 ml; 42 mmol) in anhydrous THF (90 ml), chloroacetylchloride (3.3 ml; 42 mmol) was added dropwise. The mixture was stirred at 0° C. for 2 hours, the solvent was evaporated and the residue was dissolved in ethyl acetate. The organic layer was washed with 10% aqueous HCl and diluted aqueous $Na_2CO_3$ then it was dried and evaporated. The crude residue was crystallized with n-hexane to give the title compound as a white solid. 10.8 g.

DESCRIPTION 11
2-methoxy-6-nitroaniline

To a mixture of 2-hydroxy-6-nitroaniline (41 g; 0.266 mol) and 85% KOH (17.5 g; 0.266 mol) in anhydrous DMF (80 ml), $CH_3I$ (16.5 ml; 0.266 mol) was added dropwise. The reaction mixture was stirred at room temperature for 4 hours then poured into ice-water, the title compound precipitated as a brown solid. 40 g; m.p. 67–68° C.

DESCRIPTION 12
4-methoxy-2-oxo-2,3-dihydrobenzimidazole-1-carboxylic Acid Phenyl Ester To a solution of 4-methoxy-2-oxo-2,3-dihydrobenzimidazole (24 g; 0.146 mol) in pyridine (200 ml), phenylchloroformate (18.4 ml; 0.146 mol) was added dropwise. The reaction mixture was refluxed for 14 hours then was poured into ice-water. The precipitated solid was collected and dried to give the title compound. 30 g; m.p. 204–205° C.

DESCRIPTION 13
1-(4-methoxy-3-trifluoromethylphenyl)piperazine

A mixture of 4-methoxy-3-trifluoromethylphenylamine (12 g; 0.0627 mol) and bis(2-chloroethyl) ammonium chloride (11.2 g; 0.0627 mol) in n-butanol (120 ml) was refluxed for 10 hours. The reaction mixture was cooled at room temperature and the crude title compound precipitated as hydrochloride salt overnight. The solid was collected and crystallized from acetone. 7 g; m.p. 244–245° C.

According to the above described procedure, the following compounds were prepared:

1-(3-methoxy-5-trifluoromethylphenyl)piperazine
White solid. m.p.>250° C. (as hydrochloride salt)
2-piperazin-1-yl-4-trifluoromethylphenol
White solid. m.p.>250° C. (as hydrochloride salt)

EXAMPLE 1
5-Hydroxy-1-{2-[4-(3-trifluoromethylphenyl)piperazin-1-yl]ethyl}-1,3-dihydro-benzimidazol-2-one (Compound 1)

A mixture of 5-methoxy-1-{2-[4-(3-trifluoromethylphenyl)piperazin-1-yl]ethyl}-1,3-dihydrobenzimidazol-2-one (0.6 g; 1.4 mmol) and 48% HBr (30 ml) was refluxed for 1 hour. The reaction was then cooled and water was added (30 ml). The precipitated solid was collected and recrystallized from 95% EtOH to give the title compound as a white solid 0.4 g; m.p. 275° C. (as hydrobromide salt, from 95% ethanol). $^1$H-NMR (DMSO; 200 MHz): 10.82 (1H, s); 9.6, (1H, b); 9.11(1H, s); 7.47 (1H, m); 7.2–7.4 (2H, ov); 7.16 (1H, d); 7.03 (1H, d); 6.4–6.6 (2H, ov); 4.17 (2H, t); 4.03 (2H, d); 3.82 (2H, d); 3.51 (2H, b); 2.9–3.5 (4H, ov).

According to the above described procedure, the following compounds were prepared:

6-Hydroxy-1-{2-[4-(3-trifluoromethylphenyl)piperazin-1-yl]ethyl}-1,3-dihydro-benzimidazol-2-one (Compound 2)
m.p.>250° C. (as hydrobromide salt, from 95% ethanol); $^1$H-NMR (DMSO, 200 MHz);10.73 (1H, s); 9.6 (1H, b); 9.13 (1H, s); 7.48 (1H, m); 7.2–7.4 (2H, ov); 7.16 (1H, d); 6.81 (1H, d); 6.69 (1H, d); 6.49 (1H, m); 4.18 (2H, t); 4.04 (2H, d); 3.84 (2H, d); 3.51 (2H, b); 2.9–3.5 (4H, ov).
4-Hydroxy-1-{2-[4-(3-trifluoromethylphenyl)piperazin-1-yl]ethyl}-1,3-dihydro-benzimidazol-2-one (Compound 3)
m.p. 110° C. (as hydrochloride salt, from 5% HCl) $^1$H-NMR (DMSO, 200 MHz); 10.92 (1H, s); 10.8 (1H, b); 9.83 (1H, s), 7.47 (1H, m); 7.2–7.4 (2H, ov); 7.15 (1H, d); 6.7–7.0 (2H, ov); 6.57 (1H, d); 4.25 (2H, b); 4.0 (2H, m); 3.8 (2H, m); 3.0–3.6 (6H, ov).
7-Hydroxy-1-{2-[4-(3-trifluoromethylphenyl)piperazin-1-yl]ethyl}-1,3-dihydro-benzimidazol-2-one (Compound 4)
m.p. 246° C. (as hydrochloride salt, from ethyl acetate); $^1$H-NMR (DMSO, 200 MHz); 10.95 (1H,s); 10.3 (1H, b); 10.07 (1H, s); 7.47 (1H, m); 7.2–7.4 (2H, ov); 7.15 (1H, d); 6.83 (1H, m); 6.57 (1H, d); 6.52(1H, d); 4.34 (2H, t); 3.99 (2H, m) 3.81 (2H, m); 3.56 (2H, b); 3.0–3.5 (4H, ov).
1-{2-[4-(4-Hydroxy-3-trifluoromethylphenyl)piperazin-1-yl]ethyl}-1,3-dihydro-benzimidazol-2-one (Compound 5)
m.p.>250° C. (as hydrochloride salt, from acetone); $^1$H-NMR (DMSO, 200 MHz); 11.07 (1H, s); 10.7 (1H, b); 10.1 (1H,b); 7.33 (1H, m); 6.9–7.2 (6H, ov); 4.7 (1H+HDO, b); 4.29 (2H, t); 3.6–3.9 (4H, ov); 3.5 (2H, b); 3.01 (2H, m).
1-{2-[4-(3-Hydroxy-5-trifluoromethylphenyl)piperazin-1-yl]ethyl}-1,3-dihydro-benzimidazol-2-one (Compound 6)
m.p. 170° C. (as hydrobromide salt, from 95% ethanol); $^1$H-NMR (DMSO, 200 MHz); 11.06 (1H,s); 9.97 (1H, s); 9.6 (1H, b), 7.27 (1H, m); 7.0–7.1 (3H, ov); 6.8 (1H, b); 6.6 (1H, b); 6.5 (1H, b); 4.2 (2H, b); 3.95 (2H, d); 3.81 (2H, d); 3.5 (2H, b); 2.9–3.5 (4H, ov).

EXAMPLE 2
1-{2-[4-(2-Hydroxy-5-trifluoromethylphenyl)piperazin-1-yl]ethyl}-1,3-dihydro-benzimidazol-2-one (Compound 7)

A mixture of 2-piperazin-1-yl-4-trifluoromethylphenol hydrochloride salt (0.17 g; 0.53 mmol), 80% NaH (0.03 g; 1.06 mmol), $K_2CO_3$ (0.148 g; 1.06 mmol) and 1-(2-chloroethyl)-1-3-dihydrobenzimidazol-2-one (0.104 g; 0.53 mmol), was heated at 80° C. for 4 hours. After cooling, the reaction mixture was poured into water and the separated oil was extracted into ethyl acetate. The crude title compound was purified by flash chromatography (silica gel; eluent: $CH_2Cl_2$/MeOH/$NH_4OH$ 97:3:0.3) to give the free base of the title compound. The hydrochloride salt was obtained in ethyl acetate and ethereal HCl solution. White solid. 25 mg; m.p. 158–160° C.

We claim:

1. A compound of the general formula (I)

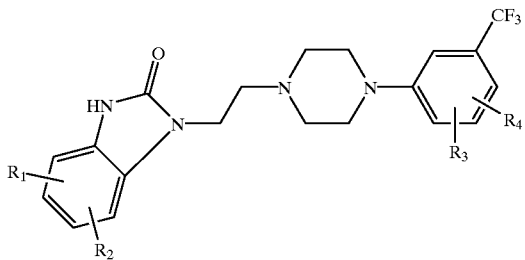

wherein:

$R_1$, $R_2$, $R_3$, and $R_4$ are each hydrogen or hydroxy, with the proviso that $R_1$, $R_2$, $R_3$, and $R_4$ cannot simultaneously represent hydrogen, or a physiologically acceptable acid addition salt thereof.

2. The compound of general formula (I) according to claim 1, wherein two or three of the four radicals $R_1$, $R_2$, $R_3$, and $R_4$ are hydrogen, or a physiologically acceptable acid addition salt thereof.

3. 5-Hydroxy-1-{2-[4-(3-trifluoromethylphenyl)piperazin-1-yl]ethyl}-1,3-dihydro benzimidazol-2-one, or a physiologically acceptable acid addition salt thereof.

4. 6-Hydroxy-1-{2-[4-(3-trifluoromethylphenyl)piperazin-1-yl]ethyl}-1,3-dihydro-benzimidazol-2-one, or a physiologically acceptable acid addition salt thereof.

5. 4-Hydroxy-1-{2-[4-(3-trifluoromethylphenyl)piperazin-1-yl]ethyl}-1,3-dihydro-benzimidazol-2-one, or a physiologically acceptable acid addition salt thereof.

6. 7-Hydroxy-1-{2-[4-(3-trifluoromethylphenyl)piperazi-1-yl]ethyl}-1,3-dihydro-benzimidazol-2-one, or a physiologically acceptable acid addition salt thereof.

7. 1-{2-[4-(4-Hydroxy-3-trifluoromethylphenyl)piperazin-1-yl]ethyl}-1,3-dihydro-benzimidazol-2-one, or a physiologically acceptable acid addition salt thereof.

8. 1-{2-[4-(3-Hydroxy-5-trifluoromethylphenyl)piperazIn-1-yl]ethyl}-1,3-dihydro-benzimidazol-2-one, or a physiologically acceptable acid addition salt thereof.

9. 1{-2-[4-(2-Hydroxy-5-trifluoromethylphenyl)piperazin-1-yl]ethyl}-1,3-dihydro-benzimidazol-2-one, or a physiologically acceptable acid addition salt thereof.

10. The physiologically acceptable acid addition salt according to claim 1, wherein the physiologically acceptable acid addition salt is the salt of hydrochloric, maleic, or fumaric acid.

11. A process for the preparation of compounds of general formula (I) according to claim 1, which comprises liberation of the hydroxy group or groups by cleavage of the corresponding protective group.

12. The process for the preparation of compounds of general formula (I) according to claim 11, wherein the protective group is methyl.

13. The process for the preparation of compounds of general formula (I) according to claim 11, wherein the deprotection of the hydroxy group is carried out by treatment with a strong aqueous acid at high temperatures.

14. The process for the preparation of compounds of general formula (I) according to claim 11, wherein the deprotection of the hydroxy group is carried out by treatment with boron derivatives at low temperatures in chlorinated solvents.

* * * * *

UNITED STATES PATENT AND TRADEMARK OFFICE
CERTIFICATE OF CORRECTION

PATENT NO. : 6,281,218 B1
DATED : August 28, 2001
INVENTOR(S) : Enzo Cereda, Maura Bignotti and Giovanni Battista Schiavi Page 1 of 1

It is certified that error appears in the above-identified patent and that said Letters Patent is hereby corrected as shown below:

Title page,
The Assignee shown as "Ingelheim Italia S.p.A" should read -- Boehringer Ingelheim Italia S.p.A. --
ABSTRACT, in the last line, after the word "pharmaceuticals" add the words, "are described herein".

Column 1,
Line 57, "an:d" should read -- and --.

Column 4,
Line 10, "TIUS" should read -- TRIS --
Line 56, "ind" should read -- and --

Column 5,
Line 23, "DMISO" should read -- DMSO --

Column 6,
Line 53, "acetami(le" should read -- acetamide --

Column 7,
Line 52, "inmoles" should read -- mmoles --

Signed and Sealed this

Ninth Day of April, 2002

Attest:

JAMES E. ROGAN
*Director of the United States Patent and Trademark Office*

*Attesting Officer*